United States Patent [19]

Kása

[11] 4,197,854
[45] Apr. 15, 1980

[54] PROCESS AND APPARATUS FOR PATIENT DANGER RECOGNITION AND FORECASTING OF A DANGER CONDITION, ESPECIALLY IN CASE OF INTENSIVE MEDICAL CARE

[75] Inventor: Zoltán Kása, Budapest, Hungary

[73] Assignee: Medicor Müvek, Budapest, Hungary

[21] Appl. No.: 871,924

[22] Filed: Jan. 24, 1978

Related U.S. Application Data

[63] Continuation of Ser. No. 595,532, Jul. 14, 1975, abandoned.

[30] Foreign Application Priority Data

Jul. 19, 1974 [HU] Hungary ................................. 10261

[51] Int. Cl.$^2$ .............................................. A01B 5/00
[52] U.S. Cl. ................................................... 128/630
[58] Field of Search ............. 128/2 R, 2.05 R, 2.05 T, 128/2.06 A, 2.06 R, 2.06 F; 340/279; 235/92 PD, 92 SH

[56] References Cited

U.S. PATENT DOCUMENTS

| | | | |
|---|---|---|---|
| 3,518,983 | 7/1970 | Jorgenson | 128/2.06 A |
| 3,618,592 | 11/1971 | Stewart | 128/2.05 R |
| 3,654,916 | 4/1972 | Neilson | 128/2.06 A |
| 3,658,055 | 4/1972 | Abe et al. | 128/2.06 A |
| 3,763,852 | 10/1973 | Hatke | 128/2.05 T |
| 3,814,082 | 6/1974 | Taylor | 128/2.05 R |
| 4,022,192 | 5/1977 | Laukien | 128/2.06 F |

Primary Examiner—William E. Kamm

[57] ABSTRACT

Process and apparatus for patient danger recognition and forecasting, particularly for the intensive medical care of the patient. The invention uses various variables to set up a danger function that represents the probability of occurrence of a danger condition, forms average values of the danger function throughout subsequent time periods that are shorter than the time required for a medical intervention, by comparing the formed average values with levels of increasing sequences of threshold values, providing an indication associated with the highest exceeded threshold value, using the average values to set up a regression function which approximates the sequence thereof, determining a subsequent extrapolated value of the function for the next time period that represents a forecast average value of the danger function, and indicating the extrapolated value provided it is higher than a predetermined level. Preferably three threshold values are used in the comparing step, with magnitudes of 40, 60 and 80% of the danger function, respectively.

11 Claims, 8 Drawing Figures

PROCESS AND APPARATUS FOR PATIENT DANGER RECOGNITION AND FORECASTING OF A DANGER CONDITION, ESPECIALLY IN CASE OF INTENSIVE MEDICAL CARE

This is a continuation of the applicant's parent application Ser. No. 595,532 filed July 14, 1975, titled "Process and Apparatus for Recognition and Forecasting for a Danger Condition, especially in case of Intensive Care", now abandoned.

The invention relates to a process and an apparatus for recognition and forecasting of a danger condition, especially in case of intensive care of patients, where quick medical intervention is necessary at the occurrence of the danger condition.

For the application of the invention, continuous attendance of the endangered patient and instrumental measurements of specified conditional characteristics are required.

It is known in medical practice that the occurrence of certain danger conditions depend on several variables, apparently independent of each other. In several cases the continuous observation of one or other of these variables is sufficient for the recognition of the danger condition because these variables can unambiguously signal the danger condition if they slip out of predetermined ranges. Such dominant variables are e.g. blood pressure, pulse rate, etc.

There are several known devices for danger recognition which are based on such dominant variables. Their operation has a common characteristic which consists in that they are signalling the danger when one of the dominant variables measured on one or another instrument falls outside a specified range.

The use of these solutions thus supposes that between the occurrence of the danger condition and the momentary values of the dominant variables measured by the instruments, there is a direct causal relationship.

The input data of the existing danger condition signalling equipments are only those conditional characteristics which are measured by instruments /such characteristics can be e.g. blood pressure, temperature, electrocardiogram, pulse rate, etc/.

There are danger conditions, however, which cannot be brought into a causal relationship with any specific "dominant" variable, which latter would alone, independently of the values of other variables, refer to the occurrence of the danger condition.

The occurrence of danger conditions of the above mentioned type is, however, a complex function of several conditional characteristics. A danger condition may still arise although the value of each individual characterizing parameter is yet within a permitted range. In such cases no danger recognition system can be used which is based on the range overrunning of certain variables.

It was recognized that the occurrence of the danger condition depends not only on instrumentally measured conditional characteristics but on data obtained from the anamnesis of the patient, on the results of observations relating to the condition of the patient reported by the attending personnel, as well as on the time elapsed since the occurrence or beginning of certain events /e.g. time of sickness, beginning of confinement, etc./. The expression "variable" is meant to stand for all of these continuous or descrete data.

In case of intensive patient care not only the occurrence of the danger condition, but the existence of a partial danger shall already be indicated, rendering thus possible the necessary medical intervention even before the occurrence of the effective danger condition.

Devices are already known to be capable to indicate a partial danger condition, which operate on the basis of the analysis of the variation tendency of dominant parameters. Such devices, however, cannot be used for applications where such dominant parameters do not exist.

It is also well known in the art that the tested measurement results may be considerably influenced by unexpected interfering effects. Although several proposals were made for the elimination of the outlined problem, none of them could safely reject the possibility of false or inappropriate danger indications.

The object of the invention is to provide a process and an apparatus suitable for the recognition and forecasting of the occurrence of danger conditions which cannot be characterized by individual dominant conditional characteristics, wherein the danger indication is not influenced by occasional disturbances, and which can also perform distinctive indications depending on the seriousness of the danger.

The invention is based on the recognition that, knowing the above mentioned variables, which together determine the occurrence of a given danger condition, a "danger function" can be set up having a momentary value which corresponds to the probability of the occurrence of the danger condition. Thus the danger function accurately represents the complex functional relationship between the above mentioned variables and the occurrence of the danger condition, therefore it can provide an appropriate basis for further signal processing steps in order to indicate a forthcoming danger condition.

Thus the danger function itself can be considered as a random variable having values ranging between 0 and 1, wherein the value 1 corresponds to a definite occurrence of the danger condition. When the danger function is set up, the duration of time which has elapsed since the beginning of a certain event or events plays an important role as a variable, because it is well known that in the human organism the actual danger condition takes place when certain time periods have passed following the occurrence of several unfavourable circumstances.

The duration of this period can also determine the time which is available for a medical intervention necessary to eliminate the danger condition.

It must be emphasized that the method by which the danger function is set up is different for each danger condition, and the invention is not limited to the evaluation of any particular danger function; the work of setting up of the danger function shall be done by experts well skilled in the art.

The invention provides a process for the recognition and forecasting of a danger condition, especially in case of intensive medical care, which danger condition is a complex function of several variables that are continuously measured conditional characteristics, data reported by the attending personnel, data obtained from the anamnesis, and data representing time durations which have elapsed since the occurrence of certain events. The inventive process is mainly characterized by the steps of using the variables to set up a danger function that represents probability of occurrence of the danger condition; forming the average or mean values of the danger function throughout subsequent time periods that are substantially shorter than the time required for the medical intervention to overcome the danger condition; comparing the formed average values with respective levels of discrete increasing predetermined sequences of threshold values; providing a specific indication associated with a highest momentary exceeded threshold value; using the discrete average values to set up a regression function which approximates the sequence thereof; determining a subsequent extrapolated value of regression function for the next time period, which represents a forecast average value of the danger function; and indicating the extrapolated value if it is higher than a predetermined level.

According to the invention an apparatus is also provided for the recognition and forecasting of a danger condition, especially for intensive medical use, in which an endangered patient is under a continuous instrumental and personal attendance, comprising handling or operating unit located in the vicinity of the patient to receive results of observances, adjusted by the attending personnel and instruments which measure specific conditional characteristics related to the occurrence of the danger condition; a danger function generator having inputs for receiving output signals of the instruments and data adjusted by the operating unit, and providing a danger function on its output, that represents, the probability of occurrence of the danger condition; an averaging unit having an input connected to the output of the generator, for averaging the danger function throughout subsequent predetermined discrete time periods; an indicating unit connected to an output of the averaging unit, for comparing the averaged values with at least one predetermined threshold value in each time period and for establishing a danger condition indication, depending on the result of the comparison; a forecasting unit connected to the output of the averaging unit, and containing a shift memory with elements for storing a given number of the subsequent averaged values obtained during the preceding time periods; the forecasting unit is serving to establish a regression function which approximates the sequence of the stored average values and to forecast the subsequent regression function, extrapolated for the next time period; and a control unit for determining the time periods; being connected to the averaging unit, and the forecasting unit.

The invention will be now described in full detail by means of examples, on the basis of the attached drawings, where FIG. 6 is a diagram of characteristic variables during an intensive childbirth delivery conduction, FIG. 7 shows a schematic circuit diagram of a danger function generator which can be used in case of an endangered birth course, and FIG. 8 shows a diagram representing the connection between the danger function and the more important parameters in case of conducting an endangered delivery.

Figure 1:
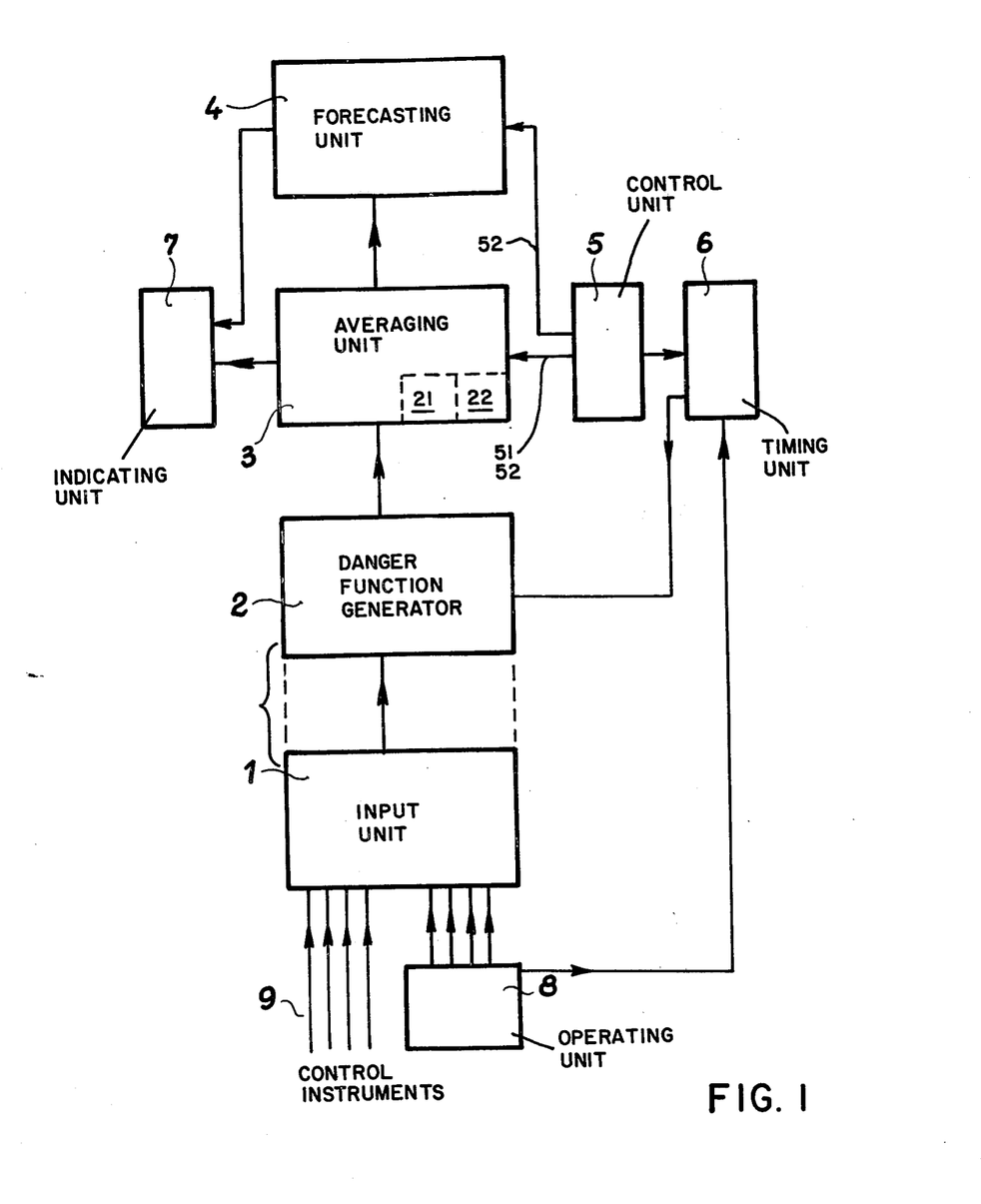
FIG. 1 is a simplified schematic block diagram of the apparatus according to the invention.
Figure 2:
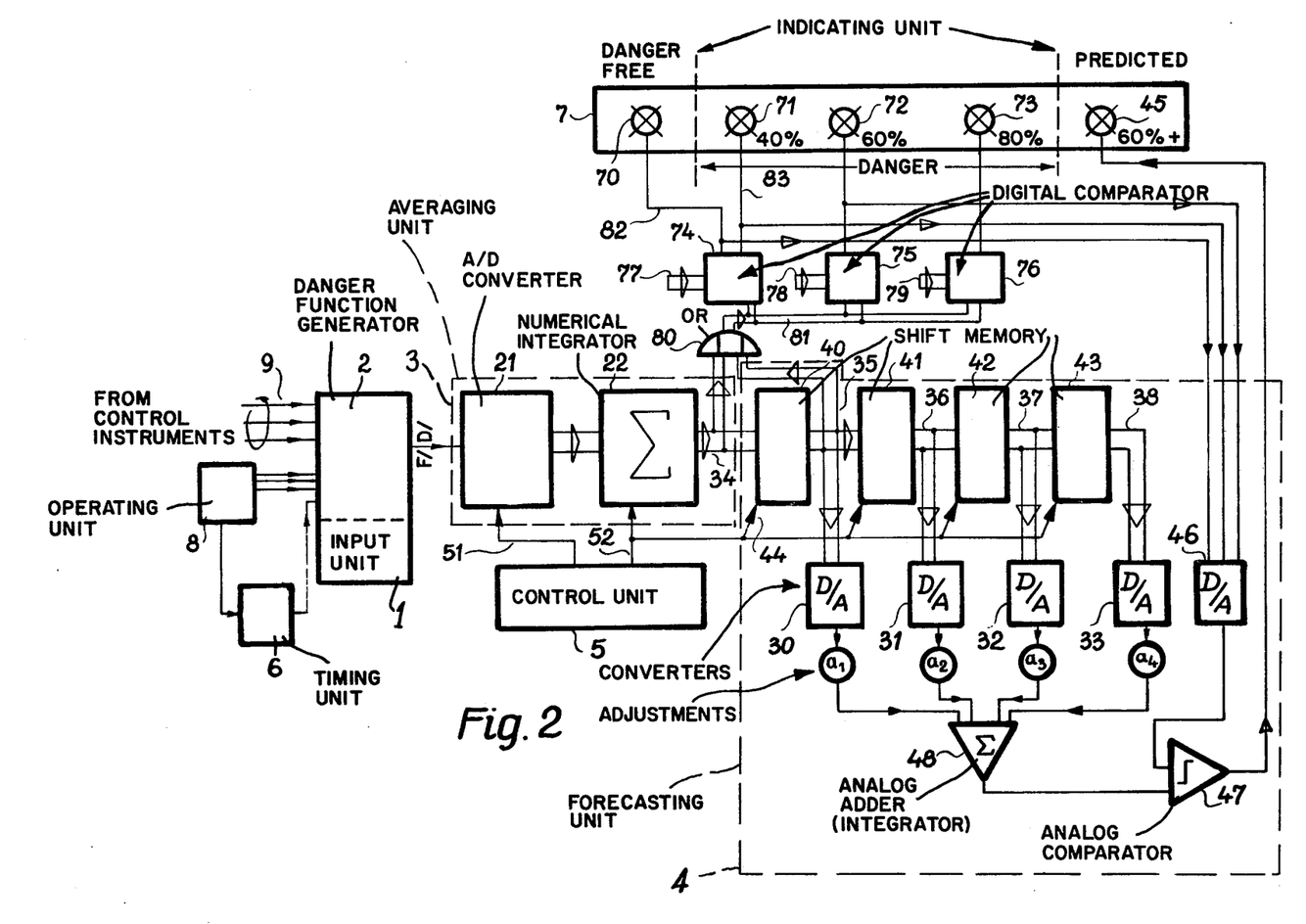
FIG. 2 is a similar but more detailed block diagram.

Reference is made now to FIG. 1 in which the block scheme of the apparatus according to the invention is shown. The apparatus comprises an input unit 1 which receives output signals of control instruments (not shown) through lines 9. The input unit 1 receives also output lines of a handling or operating unit 8 operated by the attending personnel; of a danger function generator 2 the input of which is connected to the output of the input unit 1, supplying signals at normalized levels, and possibly incorporated in unit 2, as shown in FIG. 2. There is further an averaging unit 3, averaging within given time periods the output signal of the danger function generator 2; of an indicating unit 7 which compares the output signal of the averaging unit 3 with a preadjusted sequence of treshold levels, and when the output signal exceeds these latter, it produces a distinct danger condition indication. A forecasting unit 4 is also included which uses the subsequent discrete average output signals of the averaging unit 3 to extrapolate the average value for the next time period and provides a distinct display if this extrapolated average value is higher than a predetermined threshold level; a time measuring or timing unit 6 which transmits an indication signal to the danger function generator 2, which signal is proportional to the time elapsed since the beginning of certain events adjusted by means of the handling unit or means 8; and finally a control unit 5 producing clock pulses required for the operation of the other units.

A more detailed exemplary embodiment of the apparatus according to the invention is shown in FIG. 2. For the sake of clarity the lines through which digital information flows are marked with triangular symbols, whereas the lines conducting signals are not marked.

The danger function generator 2, which will be discussed in a more detailed manner (see also FIG. 7), produces on its output a danger function F/D/ in the form of analog signals corresponding to the probability of occurrence of the danger condition. This analog signal is led to the input of an analog-digital converter 21, having the following conversion characteristic, as a consequence of which the value of the output digital number is:

0,0, if the signal $F/D/ \leq 0$ $F/D/$, if $0 < F/D/ \leq U_t$ level 1,0, if $F/D/ > U_t$.

At the digital output of the converter 21 the momentary digital value of the analog input signal F/D/ appears at the time of the sampling pulses of high repetition frequency, produced by the control unit 5 and coupled through a line 51 to the clock input of the converter 21.

This digital signal sequence is connected to the input of a numerical integrator 22 which summarizes the digital values of the signals through every subsequent time period having a duration $T_o$ determined by the clock pulses delivered via a line 52 from the control unit 5.

The duration of the periods $T_o$ is considerably longer than the cycle time of the sampling pulses but it is considerably shorter than the time of intervention required for the elimination of the given danger condition. An output 34 of the numerical integrator 22 supplies at each moment the actual summarized digital value. The numerical integrator 22 is set to zero by the clock pulses arriving from the line 52 at the end of each time period $T_o$.

Still in FIG. 2, there is coupled to the output of the numerical integrator 22 a shift memory having four memory elements: 40 to 43 which are connected in series. The drawing shows that these memory elements have outputs 35 to 38 (leading to the respective digital-analog converters 30 to 33, to which details reference will be had as the description proceeds. The clock pulses that determine the periods $T_o$ are connected to gating inputs 44 of that shift memory elements through the line 52, and each pulse causes a step forward of the stored digital values whithin the shift memory. Thus, at the output of the shift memory element $R_1$ an average value is present in the form of a digital number which has been summarized during the period $T_o$ preceding the prevailing testing moment. At the output of the second shift memory element 41 the average value appears that was produced two time periods earlier, and in this way the shift memory elements successively store the average values of the numerical integrator 22 obtained from the preceding periods.

The output of the numerical integrator 22, as well as the output of the shift memory element $R_1$ are connected to respective inputs of a digital OR circuit 80. This OR circuit 80 is arranged so that at its output always the greater number of the digital numbers conducted to its inputs appears. This digital number corresponds actually to the greatest average value of the danger function F/D/ obtained in the current and yet unfinished period $T_o$ and in the last finished period.

The output of the digital OR circuit 80 is connected (in FIG. 2) to a line 81 which is in connection with signal inputs of three digital comparators 74, 75, 76. To the respective reference inputs of these comparators threshold level adjusting elements 77, 78, and 79 are connected which are respectively preset to digital numbers corresponding to the 40%, 60% and 80% values of the danger function F/D/. These elements 77, 78 and 79 are shown schematically in the drawings.

On a signal output 83 of the digital comparator 74 an output voltage appears when the value of the digital number transmitted through the line 81 is greater than the 40% value of the danger function, but lower than the 60% value thereof. The output line 83 is in connection with an indicating unit or element organ or 71, e.g. with an orange signal lamp which gives an optical signal if the danger function falls between 40 and 60%.

A voltage signal is present on an inverse signal output 82 of the digital comparator 74 when the momentary average value and that taken for the previous interval are both lower than 40%. The output line 82 is in connection with a further indicating unit or element 70, e.g. with a green signal lamp which indicates the danger-free condition.

The signal outputs of the digital comparators 75 and 76 are connected to respective indicating units or elements, or organ 72 and 73, similar to 71, e.g. to signal lamps giving a red and a flashing red light. The display unit 72 gives signals if the aforementioned average value of the danger function falls between 60 and 80%, whereas the unit 73 signals when the average value of the danger function is higher than 80%. The circuit shown in FIG. 2 provides an appropriate, conventional electronic circuit as a result of which only that one of the indicating elements 71 to 73 is selected and operates that belongs to the highest exceeded threshold value, from among the 40, 60 and 80% indications.

In FIG. 2, the output of each shift memory element 40 to 43 is connected to a respective digital input of the four digital-analog converters 30, 31, 32 and 33 that were mentioned earlier in connection with the memory elements. Each of these its output an analog converters produce on their outputs an analogue signal proportional to the digital number stored in the corresponding memory element. The output analog signals of the converters are connected in succession to four analog level adjusting means $a_1$, $a_2$, $a_3$ and $a_4$, e.g. to potentiometers or amplifiers, through which the coefficient of the regression function can be adjusted that is necessary for the forecasting. The outputs of the level adjusting means are connected to inputs of an analog integrator or adder 48, at the output of which the danger function value predicted for the time interval following the test moment appears as an analog signal. This predicted or extrapolated value is connected to the signal input of a comparator 47.

The reference level of the comparator 47 depends on the value of the momentarily indicated danger function in the following manner. If the element 70 operates, no momentary danger exists and a digital signal corresponding to a 40% value of the danger function is passed through the line 82 to the input of a digital analog converter 46 which is connected to the reference input of the comparator 47.

If the element 71 is in operation, a signal corresponding to a 60% threshold level arrives to the input of the digital-analog converter 46 through the line 83, and if the element 72 operates, the value of the threshold level is 80%. Accordingly, a signal will only be obtained at the output of the comparator 47 if the value of the danger function predicted for the following interval is higher than the momentarily not exceeded lowest threshold value.

If, for instance, the yellow lamp burns, corresponding to a danger function ranging between 40 and 60%, an additional indicating element 45, connected to the output of the comparator 47, operates only if the predicted value of the danger function is higher than 60%.

The aspects of the establishment of the danger function are described in connection with FIGS. 3 and 4. Variables $x_1$ and $x_2$ shown in FIG. 3 determine together the occurrence of the given danger condition. The independent criteria mentioned in the introduction of the description obviously cannot be enforced either to the variable $x_1$ alone, or to the variable $x_2$ alone.

Figure 3:
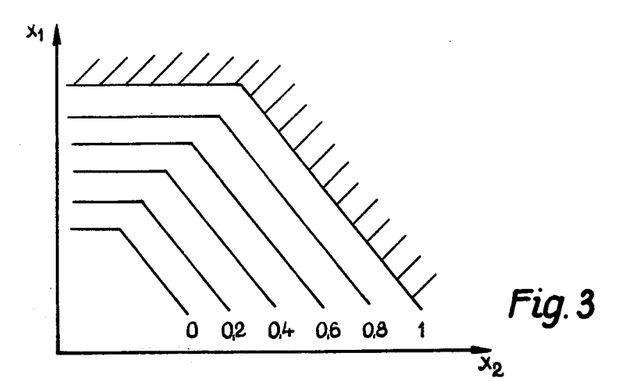
FIGS. 3 and 4 represent the complex functional relationship between different variables and a danger function.

The parameters shown in FIG. 3 indicate the probability of occurrence of the danger condition, that is the constant danger function values. In the hatched field the value of the danger function is always unity. It will be understood by those skilled in the art that the designations "0.4" ... "0.8" correspond to the earlier-explained percentages 40% ... 80%.

Figures 4, 5:
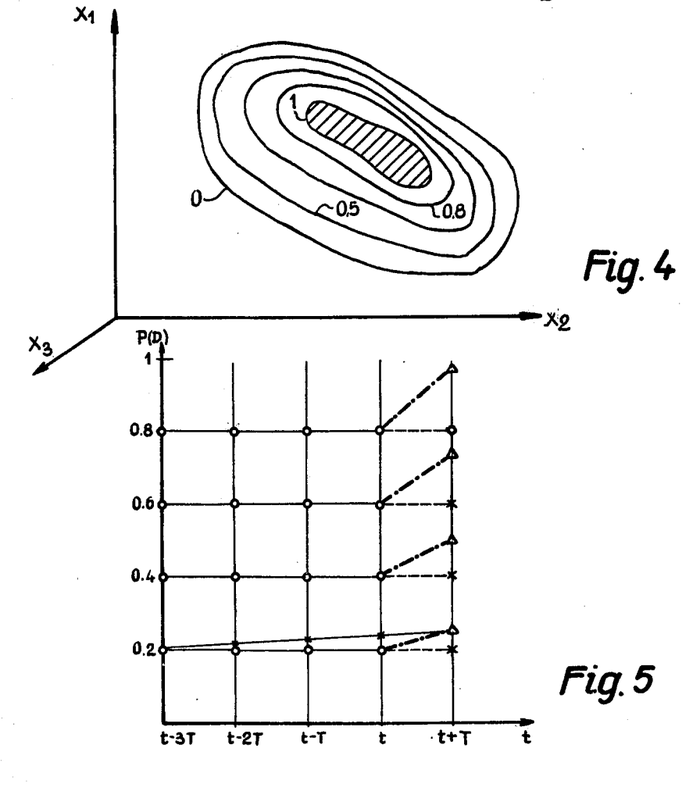
FIG. 5 is a diagrammatic representation of a distorted estimation used for the forecasting of the danger function.

In FIG. 4 a case is indicated where the occurrence of the danger condition is the common function of three variables $x_1$, $x_2$ and $x_3$ although the dependence on the variable $x_3$ is not illustrated. The shapes of the curves characterizing the constant values of the danger function are similar to the cartographic level lines. It is clear that in cases where the danger function is dependent on the complexity of all variables, neither of the particular variables can alone be brought into a direct causal relation with the danger function.

In FIG. 5 the establishment of the extrapolated averaged danger function value is shown which corresponds to a future time period $T_o$ which directly follows the moment t of the test. At the outputs of the shift memory elements 40 to 43 the averaged values of the danger function, calculated to the last four time intervals $T_o$, are available in succession. The sequence of these values is approximated by a regression function in which the square sums of deviations are kept at a minimum. For this purpose, e.g. a so-called quadratic regressive algorithm may be used.

The values of the analog level adjusting means $a_1 \ldots a_4$ shall now be adjusted as follows:

$a_1 = 2.25; a_2 = -0.75; a_3 = -1.25; a_4 = 0.75.$

The function of the predicted values is:

$F/t+T_o/ = a_1 F/t/ + a_2 F/t-T_o/ + a_3 F/t-2T_o/ + a_4 F/t-3T_o/$

It was, however, recognized that, as for the future, there may also be serious consequences if the danger function has a permanently high value for a longer period. Therefore, a modified quadratic regressive algorithm can advantageously be used, which, in case of permanently high values of the danger function, increases artificially the predicted future values of the danger function, whereby it calls attention to the intensification of an effective danger condition.

In FIG. 5 sets of averaged values of the danger function are indicated which have been obtained through subsequent preceding time periods. These values are chosen to be equal but additionally each set has different absolute values. The value forecast to the subsequent future time interval $t+T_o$ is marked with broken lines if the quadratic regressive algorithm approach is used, and with dot-dash lines if the modified algorithm is used. It is to be seen that the value of the forecast danger is taken into consideration with an increasing tendency for the modified approach, as soon as the value of the existing danger is continuously high.

The following coefficients relate to the modified quadratic regressive algorithm:

$a_1 = 2.4525; a_2 = -0.795; a_3 = -1.2875; a_4 = 0.75.$

The process according to the invention will be explained now by means of a specific example in which reference is made to FIGs. 6, 7 and 8.

In case of an intensive conduction of parturition from the point of view of the embryo, the tendency signals life danger at which the extent of the fetal heart rate /FHR/ decreases, simultaneously therewith the heart rate dip becomes larger, and the time shift between the peak value of the intrauterine pressure /IUP/ as well as the lowest point of the dip of the fetal heart rate increases.

Until now, this kind of danger was tested in such a manner that these characteristics were represented in a way corresponding to the diagram shown in FIG. 6, and the necessary conclusion was drawn form the obtained diagram. During the delivery conduction considerable time was required for the diagrammatical representation of the variables, and the results evaluated therefrom became obvious only much later when there was only a very short time available for the elimination of the danger.

It has been recognized experimentally that in the exemplary case the danger function can accurately be represented by the following relationship:

$F/D/ = -5 FHR - 7 IUP + 5 REF FHR + 0.2 T$ where

FHR—a voltage proportional to the value of the fetal heart rate, eg. 100/min=1 Volt IUP—a voltage proportional to the measure value of the intrauterine pressure (=IUP), e.g. 100 Hgmm=1 Volt.

REF FHR—the adjusted value of the fetal heart rate before the confinement, e.g. 100/min=1 Volt T—the time elapsed since the beginning of the confinement.

The above danger function is reproduced by a danger function generator, as described earlier under Ref. No. 2, shown in FIG. 7. It is to be seen that the input signals forming the variables, thus the signals FHR and IUP, as well as the time signal T are led directly to analog inputs of the danger function generator 2. With the arrangement represented in FIG. 7, the danger function generator is constituted by a differential amplifier having a feedback through a resistance R, and the inputs thereof are connected to the input signals through resistances R/5, R/7 having ohmic values chosen in accordance with the coefficients appearing in the relationship of the danger function.

The time signal T is obtained so that a switch K is closed at the beginning of the parturition and thereby the earlier-mentioned timing unit 6 is started. The switch K is manual and forms part of, or constitutes, the earlier-described operating unit 8.

FIG. 8 represents the formation of the danger function in case of a constant time T, when the signals FHR and IUP can be taken for variables.

In the examplary case the apparatus (e.g. of FIG. 2) is adjusted so that from the output signals which are continously present at the output of the danger function generator 2, a digital danger function signal is formed at every sampling moment, which occurs about every second, and the sequence of the sampled digital numbers is summarized through the subsequent periods of $T_o = 2$ to 10 minutes by means of the numerical integrator 22.

As a result of the summation that is of the average forming, the random changes of the danger function caused by noises or other disturbances cannot exert an influence on the resulting danger recognition since the short-lasting events can hardly influence the long-term averages. This feature considerably increases the reliability of the inventive process and makes it insensitive to disturbances.

It is obvious from the above example that the apparatus according to the invention not only facilitates the work of the obstetricians during the parturition when rendering unnecessary the evaluation of the conventional diagram shown in FIG. 6, but it also gives a much sooner warning about a forthcoming danger condition.

Since the digital comparators 74, 75, 76 receive not only the danger function value averaged to the time period preceding the given moment but, through the digital OR circuit SO, they receive also the partial results emerging during the momentarily still unfinished time period, unforeseen events may still produce a sudden danger condition warning also during the current, yet unfinished time period if the partially summarized value of the danger function goes beyond one of the threshold levels.

On the basis of the exemplary apparatus according to the invention it may be stated that, as compared with the known devices, it has the following advantageous properties:

—for the recognition of a given danger condition it utilizes the mutual relationship existing between several variables, enlarging thereby considerably the range of the danger conditions falling within the instrumental danger control;

—it also uses time as a variable, taking thereby into consideration the time available for a medical intervention, as a factor increasing or reducing the actual danger;

—the occurrence of the danger condition is displayed according to preadjusted danger level steps or levels, and a separate indication is provided to warn about a forthcoming future danger if the condition of the patient is expected to turn to the worse, —through averaging, non-specific signal oscillations, noises and other disturbances are filtered out; and —if the value of the danger function is relatively high throughout a considerable period, this fact is taken into consideration as an increased danger.

The apparatus according to the invention can of course be built in several forms deviating from the example shown in FIG. 2, without, however, departing from the basic idea. Thus, for example, instead of the digital-analog conversions, a fully analog system can also be used, or any other suitable modification can be carried out. The invention should not be limited therefore to the embodiments introduced by way of examples.

What I claim is:

1. A process for the recognition and forecasting of a possible danger condition, especially for intensive medical care where an endangered patient is under continuous instrumental and personal attendance, which danger conditions is a complex function of several variables that are continuously measured specific conditional characteristics, data reported occasionally by the attending personnel, data obtained from the anamnesis, and data representing time durations that have elapsed since the occurrence of certain events, the process comprising the steps of: using the variables to set up a danger function that represents the probability of occurrence of the danger condition; forming discrete average values of the danger function throughout subsequent predetermined discrete time periods that are substantially shorter than the average time required for a medical intervention, known to be between 2 and 10 minutes, to overcome the danger condition; comparing the formed average values with respective levels of discrete increasing predetermined sequences of threshold values; providing an indication associated with a highest momentaneous exceeded threshold value; using the discrete average values to set up a regression function which approximates the sequence thereof; determining a subsequent extrapolated value of the regression function for the next time period that represents a forecast average value of the danger function; and also indicating the extrapolated value provided it is higher than a predetermined level which latter corresponds to at least the lowest one of the threshold values; which lowest value has not been exceeded during said comparing step.

2. The process as defined in claim 1 further comprising the repetition of, wherein said comparing step with three of the threshold values, the magnitudes of which correspond in succession to 40, 60 and 80% values of the danger function, respectively.

3. An apparatus for the recognition and forecasting of a possible danger condition, especially for intensive medical care, where an endangered patient is under continuous instrumental and personal attendance, comprising, in combination: an operating unit (8) located in the vicinity of the patient, to receive results of observances, adjusted by the attending personnel, and from instruments that measure specific conditional characteristics related to the occurrence of the danger condition; a danger function generator (2) having inputs (9) for receiving output signals of said instruments and for providing a danger function (F/D/) at its output that represents the probability of occurrence of the danger condition; an averaging unit (3) having an input connected to said generator output, for averaging the danger function throughout subsequent predetermined discrete time periods; digital comparator means (74 to 76) connected to an output (80) of said averaging unit, for comparing the average values with at least one predetermined threshold value in each time period; an indicating unit (7, 45, 70) connected to signal outputs (82, 83) of said comparator means, for giving indications of degrees of the danger condition, depending on said comparator outputs; a forecasting unit (4) also connected to said averaging output, including a shift memory (40 to 43) having at least two memory elements for storing a number of the subsequent average values obtained during the preceding predetermined time periods; said forecasting unit serving to establish a regression function which approximates the sequence of the stored average values and to forecast by an indication via an additional element (45) of said indicating unit, by way of D/A conversion, analog addition and comparison in elements (46, 48, 47) of said forecasting unit, a subsequent extrapolated value of the regression function for the next time period; and a control unit (5) for determining the time periods, being connected to said averaging unit and said forecasting unit.

4. The apparatus as defined in claim 3, further comprising a time-measuring unit (6) for delivering a signal that is proportional to the time duration that has elapsed since the beginning of an event adjusted by the attendant personnel, said operating unit (8) being operatively connected with said measuring unit, the output of which latter is connected to one of said input unit (1) and said danger function generator (2).

5. The apparatus as defined in claim 3, further comprising in said averaging unit (3) an A/D converter (21) and a numerical integrator (22) for summarizing discrete values of the danger function, sampled by clock pulses having a considerably shorter cycle time than the predetermined time periods, said danger function generator (2) being connected to said averaging unit through said converter, and wherein said control unit (5) has an output (52) for delivering the clock pulses, being connected to a clock-signal input of said integrator.

6. The apparatus as defined in claim 5, wherein said comparator means (74 to 76) has inputs (81) that are parallel-connected and controlled by way of said averaging output (80), from an output (34) of said integrator (22), by the integrated value of the danger function, said comparator means having at least two units (74 to 76) therein with separate reference inputs, with means (77 to 79) connected to said comparator units for adjusting the differring threshold values that correspond to successive and increasing ones of the discrete values of the danger function, said comparator signal outputs (82, 83) being led to elements (71 to 73) of said indicating unit (7, 45, 70), each associated with a predetermined danger level, wherein an inverse output (82) of one (74) of said comparator units, being associated with the lowest danger level, is a further element (70) of said indicating unit for dinstinctively signalling a danger-free condition.

7. The apparatus as defined in claim 6, wherein said adjusting means (77 to 79) serves to provide threshold values of 40, 60, 80% values of the danger function, respectively, for three of said comparator units (74 to 76).

8. The apparatus as defined in claim 6, wherein said comparator means has three units (74 to 76) therein, respectively connected to said indicating elements (71 to 73), and electronic selecting means as an effect of which only that one of said elements operates that belongs to the highest exceeded threshold value.

9. The apparatus as defined in claim 6, further comprising in said forecasting unit (4) D/A converters (30 to 33), analog-level adjusting means ($a_1$ to $a_4$) for adjusting coefficients of the regression function, and an analog adder (48) which furnishes an extrapolated average value of the danger function that corresponds to the next time period, wherein an input of one (40) of said shift-memory elements (40 to 43) is connected to said integrator output (34), and individual outputs (35 to 38) of said memory elements are coupled through respective ones of said converters to said adjusting means, outputs of the latter means being connected to respective inputs of said adder.

10. The apparatus as defined in claim 9, further comprising a digital OR circuit (80) at said averaging output, said circuit having a first input connected to said integrator output (34), a second input connected to an output (35) of said one (40) shift-memory element, and outputs of said circuit constituting said comparator inputs (81).

11. The apparatus as defined in claim 9, further comprising in said forecasting unit (4) an analog comparator (47) having a reference input and a D/A converter (46), wherein an output of said analog adder (48) is connected to a signal input of said comparator, said input of the latter being coupled to an output of said converter, the latter having inputs connected to said inverse output (82) and to a signal output (83) of said one (74) comparator unit, as well as to a signal output of another one (75) of said comparator units (74 to 76), respectively, and an output of said analog comparator is coupled to said additional element (45) of the indicating unit (7, 45, 70), for producing a distinctive indication of a forecast danger condition.

* * * * *